United States Patent [19]

Peterson et al.

[11] Patent Number: 5,350,625
[45] Date of Patent: Sep. 27, 1994

[54] ABSORBENT ACRYLIC SPUNLACED FABRIC

[75] Inventors: Robert H. Peterson; James T. Summers, both of Hendersonville

[73] Assignee: E. I. Du Pont de Nemours and Company, Wilmington, Del.

[21] Appl. No.: 89,871

[22] Filed: Jul. 9, 1993

[51] Int. Cl.$^5$ .............................................. B32B 5/06
[52] U.S. Cl. .................................... 428/219; 5/484; 5/500; 428/284; 428/288; 428/297; 428/298; 428/299; 428/913; 604/358; 604/365; 604/374
[58] Field of Search ............... 428/224, 284, 288, 297, 428/298, 299, 369, 370, 398, 913; 604/358, 365, 374; 5/484, 500

[56] References Cited

U.S. PATENT DOCUMENTS

| | | | |
|---|---|---|---|
| 3,485,709 | 12/1969 | Evans et al. | 161/109 |
| 4,664,959 | 5/1987 | Dagenais et al. | 428/74 |
| 4,808,467 | 2/1989 | Suskind et al. | 428/299 |
| 4,835,042 | 5/1989 | Dohzono et al. | 428/299 |
| 4,929,498 | 5/1990 | Suskind et al. | 428/299 |
| 4,931,355 | 6/1990 | Radwanski et al. | 428/299 |
| 5,085,653 | 2/1992 | Levy | 604/358 |
| 5,093,190 | 3/1992 | Kwok et al. | 428/288 |
| 5,151,320 | 9/1992 | Homonoff et al. | 428/299 |
| 5,240,764 | 8/1993 | Haid et al. | 428/299 |

FOREIGN PATENT DOCUMENTS

| | | |
|---|---|---|
| 3515580A | 11/1985 | Fed. Rep. of Germany . |
| 60-027530A | 2/1985 | Japan . |
| 62-299501A | 12/1987 | Japan . |
| WO92/03999 | 3/1992 | PCT Int'l Appl. . |

*Primary Examiner*—James J. Bell

[57] ABSTRACT

Spunlaced fabric having improved water absorbency containing a blend of certain hydrophilic cellulosic and acrylic fibers and layered absorbent materials made therefrom.

13 Claims, No Drawings

ABSORBENT ACRYLIC SPUNLACED FABRIC

BACKGROUND OF THE INVENTION

1. Field of the Invention

This invention relates to a water-absorbent cellulosic-/acrylic spunlaced fabric having improved wickability and water retention capabilities, composite water-absorbent sheet materials and articles made therefrom, and the use of such materials and articles to protect other materials from damage by water and aqueous soiling, especially such as hospital bedding.

2. Description of the Related Art

Water-absorbent spunlaced fabrics of synthetic acrylic and cellulosic fibers, and a method for their manufacture, are known for use in reusable diapers as taught, for example, in U.S. Pat. No. 3,485,709 (Evans). Absorbent spunlaced fabrics, and their manufacture, of acrylic and polyester fibers useful as wipers, coverstock for sanitary napkins, diapers, and the like are known as taught, for example, in U.S. Pat. No. 5,093,190 (Kwok et al.). Reusable, washable, multilayered urine-absorbent, bed pads having a soft pervious outer sheet, and an impermeable outer sheet, with a non-woven layer of absorbent material, such as a mixture of rayon and polyester fibers, in between is known from U.S. Pat. No. 4,664,959 (Dagenais et al.). Another reusable incontinent underpad is the subject of U.S. Pat. No. 5,085,653 (Levy) comprising a pervious woven or knit fabric layer, a nonwoven absorbent layer and an impervious film layer. The absorbent layer can be a blend of polyester, rayon, or 100% polyester, rayon, or cotton.

Improvements in the wickability and liquid retention capabilities of absorbent fabrics for such applications continue to be sought in an effort to provide more effective protection and comfort in use. This is especially true concerning reusable hospital bed pads for incontinent adult patients, where the weight of the patient tends to cause pooling of the urine beneath the patient, which is not readily wicked away by presently used bed pads. Present pads, for example, may consist of a woven polyester/cotton top layer, an internal absorbent layer of polyester or polyester/rayon in a nonwoven fabric, a urethane or vinyl waterproof bottom sheet to which is bonded a knit polyester or nylon fabric to provide a non-slip surface on the bed, as taught in U.S. Pat. No. 5,085,653 (Levy).

SUMMARY OF THE INVENTION

This invention provides an improved spunlaced water-absorbent fabric comprised of a mixture of acrylic and synthetic cellulosic fibers wherein the improved fabric consists essentially of about 25 but less than 50 percent, by weight, of crimped acrylic fibers having a denier per filament (dpf) of about 0.75 to about 3.0 and a length from about 0.75 to about 3.0 inches and complementally about 75 to more than 50 percent of crimped, synthetic, hydrophilic cellulosic fibers having a dpf of from about 0.75 to about 3.0 and a length from about 0.75 to about 3.0 inches.

More preferably, for best water-wicking and retention properties and desired fabric bulk the fabric consists essentially of 30 to 40% of the acrylic fibers and correspondingly 70 to 60% of the cellulosic fibers and has a basis weight of 3.0 to 5.0 oz/yd$^2$. For best performance, the cellulosic fibers consist essentially of solvent spun unmodified cellulose, as opposed to those made using regenerated xanthated cellulose, commonly known as viscose rayon. The "unmodified" cellulosic fibers are preferably of substantially round cross-section to achieve the best overall performance of wicking and bulk.

Such fabrics have been found to provide an outstanding combination of absorbent properties including high wick rates and essentially quantitative liquid retention as compared to similar combinations of cellulosic and polyethylene terephthalate fibers, and fabrics of 100% of the same cellulosic fibers. The fabric preferably is sufficiently entangled to provide integrity through wash cycling in normal use. This can be achieved while minimizing the loss of fabric thickness by using wider spaced jets in the manufacturing process at lower pressure.

Both the synthetic hydrophilic cellulosic fibers and the acrylic fibers are preferably of substantially round cross-section for the best wicking and retention performance, although non-round fibers, such as those having a known crenulated cross-section can be used.

DETAILED DESCRIPTION OF THE INVENTION

The acrylic fibers of this invention are comprised of polymers and copolymers of polyacrylonitrile, such as available commercially under the trademarks such as "Orlon", "Creslan" and "Acrilan".

The cellulosic fibers can be any hydrophilic, synthetic cellulose-based fiber such as viscose rayon but preferably are of solvent spun cellulose such as "lyocel" sold by Courtaulds Corporation.

For use in hospital bed pads for incontinent patients it is preferred that the acrylic fibers in the absorbent fabric contain a biocide, for example, one commercially known as "Microban", which can be introduced in the acrylic polymer solution during spinning. Biocide-containing acrylic fibers are commercially available, for example, "Biocryl" from the Mann Industrial Company. For use in hospital applications such as in bed pads, it is preferred that a biocide, or antimicrobial agent, be used that kills MRSA bacteria, i.e., methicillin resistant *Staphyloccocus aureus*.

The absorbent spunlaced fabrics of this invention can be prepared by methods known in the art as taught, for example, in U.S. Pat. No. 3,485,709 (Evans) and 5,093,190 (Kwok et al.), mentioned above, the entire disclosures of which are incorporated herein by way of reference.

Useful, but non-limiting, absorbent articles which can incorporate the absorbent fabric of this invention can be constructed as described for example in U.S. Pat. Nos. 5,085,653 (Levy) and 4,664,959 (Dagenais et al.), the entire disclosures of which are incorporated herein by way of reference. Other applications include protective absorbent sheet, bandage, and garment structures incorporating the subject absorbent fabrics and other uses of highly absorbent synthetic fabrics as already known in the art.

Typically, a 4.0 oz/yd$^2$ fabric of the invention is made at 13 YPM windup speed to give a 5.4 lbs/in/hr rate of production. The jet profile is optimized for that throughput and can be adjusted as the speed or basis weight are changed. Important features of the jet profile are preferably the use of 7 mil jets spaced at 10 per inch to provide the first effective needling (in consolidation) and their use in the "power" positions to effect most of the real entanglement (this provides bulk and integrity which can be hard to get with smaller bore jets and more closely spaced jets.) Typical needling jet profiles for hydroentangling the absorbent layers of this invention on conventional apparatus are shown in Table I.

TABLE I

| POSITION | NO. | JET SIZE MILS | HOLES/INCH NO. | PRESSURE PSIG |
|---|---|---|---|---|
| CONSOLIDATOR | 1 | 7 | 10 | 800 |
| CONSOLIDATOR | 2 | 7 | 10 | 750 |
| WASHERBELT | 1 | 5 | 40 | 400 |
| WASHERBELT | 2 | 5 | 40 | 600 |
| WASHERBELT | 3 | 5 | 40 | 800 |
| WASHERBELT | 4 | 5 | 40 | OFF |
| WASHERBELT | 5 | 7 | 10 | 1800 |
| WASHERBELT | 6 | 7 | 10 | 1800 |
| DRUMWASHER | 1 | 5 | 40 | 400 |
| DRUMWASHER | 2 | 5 | 40 | 600 |
| DRUMWASHER | 3 | 5 | 40 | 800 |
| DRUMWASHER | 4 | 5 | 40 | OFF |
| DRUMWASHER | 5 | 7 | 10 | 1800 |
| DRUMWASHER | 6 | 7 | 10 | 1200 |

Each of the 7/10 jets provides 0.30 horsepower hour-pounds force per pound of fabric (vs. 0.20 for "stable fabric") and at 1" of jet distance is in excess of 1 MM poundals per square inch second energy flux, using the calculations shown by Kwok in U.S. Pat. No. 5,093,190.

WASHER IMPACT TIMES ENERGY (IXE) AND JET FLOW CALCULATION

| BASIS WT. | 4.00 OZ/YD$^2$ | LINE SPEED | 13 YDS/MIN |
|---|---|---|---|
| PIH | 5.42 | JET LENGTH | 57 IN |
| (LBS/IN-HR) | | LINE | 4 |

BELT WASHER

| POSITION | DIAMETER | TYPE | PRESSURE | IXE | GPM |
|---|---|---|---|---|---|
| 1 | 5 | 40 | 400 | 0.15 | 20 |
| 2 | 5 | 40 | 600 | 0.41 | 25 |
| 3 | 5 | 40 | 800 | 0.84 | 28 |
| 4 | 5 | 40 | 0 | 0.00 | 0 |
| 5 | 7 | 10 | 1800 | 6.09 | 21 |
| 6 | 7 | 10 | 1800 | 6.09 | 21 |
| | | | TOTALS | 13.57 | 115 |

DRUM WASHER

| 1 | 5 | 40 | 400 | 0.15 | 20 |
|---|---|---|---|---|---|
| 2 | 5 | 40 | 600 | 0.41 | 25 |
| 3 | 5 | 40 | 800 | 0.84 | 28 |
| 4 | 5 | 40 | 0 | 0.00 | 0 |
| 5 | 7 | 10 | 1800 | 6.09 | 21 |
| 6 | 7 | 10 | 1200 | 2.21 | 17 |
| | | | TOTALS | 9.69 | 111 |

OTHER JETS

| CONS. NO. | 7 | 10 | 800 | — | 14 |
|---|---|---|---|---|---|
| CONS. NO. | 7 | 10 | 750 | — | 13 |
| | | | TOTAL IXE = | | 23 |
| | | | TOTAL FLOW = | | 253 |

DESCRIPTION OF TEST METHODS USED

The Absorbent Capacity is the numerical average of the GATS absorbency and the intrinsic absorbency reported as a percent. These measurements are averaged to get a number for a "partially loaded" fabric since the intrinsic absorbency is not under a load and the GATS uses about 350 kg per square meter loading.

The 80% Absorbency Challenge method uses 80% of the absorbency reported to challenge the fabric with artificial urine at 100° F. and then see how much is lost on vertical suspension for one minute.

Wick Rate is measured by the INDA STM 10.1 method.

Heat Loss is the cooling rate in °F. on challenging the bedpads with 80% of their capacity in artificial urine at 100° F.

Details are as follows:

GRAVIMETRIC ABSORBENCY TESTER (GATS), % ABS.

Equipment: Gravimetric Absorbency Tester from M&K systems or equivalent. Die of 2" diameter and a 2" diameter weight of 712 grams, flat on the bottom.

Procedure: Cut out four 2" diameter samples from product. Allow the samples to condition in the lab at 72° F. and 50% RH a minimum of 4 hours. Weigh the samples to the nearest 0.001 gram and record.

Set up GATS apparatus and set range to 20 g and print point to 0.02 g.

After pressing "yes" to start, place the sample and weight on the plate above the single orifice at the same time, allow to run until weight loss on the balance stops, usually less than 1 minute and 30 seconds.

Calc.: 100×GATS weight/sample weight=% ABS.

INTRINSIC ABSORBENCE

Cut out 2 strips of product 1"×8" each. Measure 3.5" from each end of strip and mark on opposite sides. Cut strip going from mark to mark. This will give two samples per strip that are 4.5" long measured to the point.

Weigh each sample to the nearest 0.0001 gram. Suspend the sample at the farthest corner from the acute point and immerse in water. (Water should be at room temperature, about 72° F.) Allow to soak for 1 minute, remove and allow to drain for a minute. Immediately weigh to nearest 0.0001 gram and record.

Calc.: 100×(grams wet—grams dry)/grams dry=% ABS. Take an average of 4 results minimum.

LIQUID RETENTION TESTING (80% CHALLENGE TEST)

Equipment: 400 ml beaker, 100 ml burette, 125 ml separatory funnel, thermometer referenced to NBS, lab stands, burette holder, ring holder ( for separatory funnel), 6" watch glasses, 90° clamp and 12" rod, stopwatch or lab timer, blotter paper cut into 5.75" circles.

Reagent: Artificial urine.

Procedure: Set up first ring stand with burette holder near top and ring holder near bottom so that the separatory funnel is 1" above the base and the burette drains into the funnel. Set up the second ring stand beside the first with a rod parallel to and about 12" above its base. Place a watch glass centering under the separatory funnel and under the horizontal bar. Set up a stopwatch or timer close by.

The product to be tested should have been washed at least twice. Cut 6" square samples from the bedpad, 5 per item and weigh; use the average weight to calculate the challenge. [(Int. ABS+GATS ABS)/200]×0.8-0×avg. weight=ml challenge. Weigh the blotter paper disk to 0.01 gram and place in the watch glass under the horizontal bar. (Note: Up to three of the disks may be needed, depending upon liquid not retained.)

Heat artificial urine in the 400 ml beaker to 42° C. Fill the burette with it and deliver the calculated ml challenge to the separatory funnel. Place the thermometer into the separatory funnel. When the temperature drops to 38° C. drop the liquid onto a sample fabric and start timer; drop time should be less than 1 minute.

After 2 minutes elapsed time hang the sample by one corner over the blotter disk. Small binder clips can be used to do this. Suspend for 1 minute then quickly remove. Weigh the blotter. Calculate the weight lost to the blotter. [(wet weight—dry weight)/ml delivered]×100=% loss.

WICKING RATE METHOD (FROM INDA STM)

Apparatus: Glass beaker—250 ml capacity, indelible pencil, ruler, stopwatch.

Test Specimens: Cut 3 strips 25 mm (1 in.) wide and 100–150 mm (4–6 in.) long with the long dimension in the machine direction. Cut an additional 3 specimens with the long direction in the cross direction. Mark each strip with an indelible pencil 3 nun ($\frac{1}{8}$ in.) and 28.4 mm (1$\frac{1}{8}$ in.) from one end.

Procedure: Clamp the strips at the unmarked end so that they hang vertically. Lower the strips into the beaker containing approximately 100 ml of distilled water at 21±1.1° C. (70°±2° F.) immersing them to the 3 mm ($\frac{1}{8}$ in.) mark. With a stopwatch record the time for the water to rise 25.4 mm (1 in.). Alternatively measure the height in millimeters to which the water rises in 5 minutes.

Calculation and Report: Average the results of 3 tests in each direction and report the results for each.

HEAT LOSS TEST

Purpose of Test: Determine the rate at which a given liquid will dissipate heat over a period of time from sample fabrics.

Equipment: Minolta/Land Cyclops, Compac 3 IR Thermometer and compatible data logger or comparable. An NBS 160° referenced thermometer, 100 ml burette, 100 ml beakers, 400 ml beakers, 6" diameter watch glasses, 14"×14"×1" styrofoam block, a 32" wide×24" deep×12" high board enclosure open on the top and from (to cut down drafts).

Reagents: Artificial urine.

Procedure: Ensure product samples have been through at least 2 wash cycles. Cut out the samples as 5.75" diameter circles and allow to condition in the lab at 72° F. and 50% RH for at least 4 hours. Weigh 5 samples to the nearest 0.01 gram and average the weight. Use this average as a base for the determination of 80% of the fabrics capacity as follows: [(Int. ABS+GATS ABS)/200]×0.80×average weight=ml where ml is the milliliters of artificial urine to be used.

Heat artificial urine to 42° C. Pour about 50 ml into a burette and dispense the required ml into a 100 ml beaker. Using a mercury thermometer, allow the liquid to cool to 38° C. then immediately pour onto the sample laid on a watch glass, setting on the styrofoam block. Start the data logger attached to the IR thermometer which is aimed on the center of the sample from 24" distance. Collect data on the IR temperature on 10 second intervals for 5 minutes.

Test a minimum of 3 samples and average the results. Use the temperature loss at selected intervals to characterize the cooling.

ARTIFICIAL URINE RECIPE

| Urine | % |
|---|---|
| Urea | 1.94 |

-continued

| Urine | % |
|---|---|
| Sodium Chloride | .80 |
| Magnesium Sulphate | .10 |
| Calcium Chloride | .06 |
| Water | 97.10 |

An example of a preferred article using a fabric of this invention is a bed pad having a first layer of an open mesh, circular knit, raschel or tricot fabric of hydrophobic polyester, or polyolefin (e.g., polyethylene or polypropylene) fibers, and weighing 1.5 to 3.5 oz/yd$^2$. The knit should be soft, pliant, and comfortable to a patient and have cover sufficient to minimize strikeback. Suitable commercially available pervious fabrics are "Coolmax" farbic by Deer Creek Fabrics, Stamford, CN and "Taltech" polypropylene fabric by D. V. Talbott Co., Minneapolis, MN. Two layers of a spunlaced absorbent fabric of the invention are used, as the absorbent inner layer, which contain 33% by weight round acrylic fibers containing an effective amount, i.e., less than 1%, of an antimicrobial agent for MRSA bacteria and 67% round, solvent spun, unmodified cellulosic fiber, such as "Tencel", and having a basis weight of 4.0 oz/yd$^2$. A waterproof barrier layer is used which, to reduce slippage against a bed sheet, has a brushed or unbrushed tricot or single knit polyester fabric laminated to its outer surface a vinyl or polyurethane film; such as 6 oz/yd$^2$ vinyl sheet and a 2.2 oz. polyester jersey knit fabric laminate.

The two spunlaced layers and first knit layer can be sewn together in parallel straight lines running in one direction several inches apart as needed. This composite layer is also outer seam sewn with rounded corners.

The final pad composite, if desired, can be dot-adhesively laminated so that the former tri-layer composite and the latter vinyl/knit laminate become an integral composite structure having the desired integrity, such as to endure multiple laundry washing cycles.

The performance of a bed pad using an absorbent fabric of this invention is compared with two commercially used pads. The test pad of the invention is as described above. One control for the test was a commercialpad made by "Medline". Another control for comparison was a pad made by "Dundee". After two washings the pads are tested with the following results:

| Pad Type | Test | Medline | Dundee |
|---|---|---|---|
| Absorbence Capacity, % | 410 | 397 | 310 |
| Absorbence, 80% challenge, % loss | 4.2 | 22.2 | 23.6 |
| Wick rate, seconds/inch | 2.8 | 14.8 | 13.6 |
| Heat Loss, °F. | | | |
| 1 minute | 6.7 | 5.0 | 5.6 |
| 3 minutes | 12.2 | 10.5 | 10.9 |
| 5 minutes | 15.5 | 13.4 | 14.2 |

EXAMPLE

A spunlaced, water-absorbent fabric is prepared by making a blend of 35% by weight of 2.2 decitex, 25.4 mm long, crimped, antimicrobial "Biocryl" acrylic fiber and 65% by weight of 1.7 decitex, 25.4 mm, crimped "Tencel" solvent-spun, unmodified cellulosic fibers having a substantially round cross-section. The blend is formed into a web and subjected to a hydroentangling process of the type taught in U.S. Pat. No. 3,485,709 (Evans) using a water jet profile substantially as shown in Table I. The resulting fabric is stable to disentanglement and has a basis weight of 150 grams per square meter (GSM) and is over 1.0 mm thick.

Using the absorbent fabric, a bedpad is constructed in which two layers of the absorbent fabric are plied with a top layer of a warp knit fabric of hydrophobic polypropylene fibers containing apertures between the knit yarns of about 0.9 to 1.0 mm, effective diameter at a density of 25 apertures per $cm^2$. The three layers are stitched together along the length of the composite with stitching at a spacing of about 9 to 10 cm and outer seam sewn with rounded corners in a bedpad size and shape.

A bottom sheet layer is attached to the 3-layer composite only at the edges which sheet layer has a basis weight of about 280 GSM. Of this, about 25 GSM is from a stabilized knit fabric of polyester filaments laminated to a sheet of plasticized polyvinylchloride, such as "Vintex" which can withstand laundrying but still be soft.

In tests with incontinent adult hospital patients, the pad is found to provide improved absorbency, with better wicking and less pooling, and stays cooler as compared to commercially used bedpads involving absorbent combinations of rayon and polyethylene terephalate fibers.

What is claimed is:

1. An improved spunlaced water-absorbent reusable fabric suitable for use to absorb fluid, be laundered and reused to absorb fluid again, wherein the improved fabric comprises a mixture of acrylic and synthetic cellulosic fibers and more particularly wherein the improved fabric consists essentially of about 25 to less than 50 percent, by weight, of crimped acrylic fibers having a dpf of about 0.75 to about 3.0 and a length from about 0.75 to about 3.0 inches, and about 75 to together than 50 percent of crimped, synthetic, hydrophilic cellulosic fibers having a dpf of about 0.75 to about 3.0 and a length from about 0.75 to about 3.0 inches.

2. The fabric of claim 1 having a basis weight of from about 3.0 to 5.0 ounces per square yard.

3. The fabric of claim 1 in which the fibers have a substantially round cross-section.

4. The fabric of claim 1 consisting essentially of 30 to 40% acrylic fibers and correspondingly 70 to 60% solvent-spun cellulosic fibers.

5. The fabric of claim 4 wherein both types of fibers have a dpf within the range of about 1.0 to 3.0.

6. An absorbent, composite, multilayered, reusable sheet material suitable for use to absorb fluid, then be cleaned such as by laundering, and then be reused again to absorb fluids, wherein the reusable sheet material is comprised of first and second outer layers and a water absorbent inner layer positioned between said two outer layers, wherein said first outer layer is comprised of a liquid water-permeable fabric of hydrophobic synthetic fibers, and the second outer layer is comprised of a flexible, liquid water-impermeable plastic sheet material, and the water-absorbent inner layer is comprised of a spunlaced, water absorbent fabric consisting essentially of a mixture of acrylic and synthetic cellulosic fibers wherein about 25 to less than 50 percent, by weight, are crimped acrylic fibers having a dpf of about 0.75 to about 3.0 and a length from about 0.75 to about 3.0 inches, and about 75 to greater than 50 percent of crimped, synthetic, hydrophilic cellulosic fibers having a dpf of about 0.75 to about 3.0 and a length from about 0.75 to about 3.0 inches.

7. The sheet material of claim 6 wherein the water-absorbent inner layer is comprised of at least two layers of a fabric of claim 1.

8. The sheet material of claim 7 in the form of a bed pad for protecting bedding from urinary soiling by a bed occupant, and keeping the patient dry to promote healthy skin.

9. The fabric of claim 1 wherein at least some of the acrylic fibers contain an effective amount of an antimicrobial agent.

10. The layered sheet material of claim 6, wherein the inner layer consists essentially of two layers of said fabric of 30 to 70% acrylic fibers and correspondingly 70 to 30% cellulosic fibers.

11. The use of a fabric of claims 1-5 as an absorbent layer in a bedpad.

12. A layered sheet material of claim 6 wherein the liquid water permeable first outer layer is chemically of physically treated to enhance its liquid water permeability.

13. The fabric according to claim 9, wherein said antimicrobial agent is introduced into the acrylic polymer solution during spinning said acrylic fibers.

* * * * *